US012788325B2

(12) United States Patent
Cote et al.

(10) Patent No.: US 12,788,325 B2
(45) Date of Patent: Nov. 10, 2026

(54) INTEGRATED PRESSURE TRANSDUCER FOR PRECISE QUANTIFICATION OF APPLIED SURFACE FORCE IN WEARABLE DEVICES

(71) Applicant: THE TEXAS A&M UNIVERSITY SYSTEM, College Station, TX (US)

(72) Inventors: Gerard Cote, College Station, TX (US); Justin Mcmurray, College Station, TX (US); Samuel Idah-Oze, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 245 days.

(21) Appl. No.: 18/404,959

(22) Filed: Jan. 5, 2024

(65) Prior Publication Data

US 2024/0225546 A1 Jul. 11, 2024

Related U.S. Application Data

(60) Provisional application No. 63/437,421, filed on Jan. 6, 2023.

(51) Int. Cl.
*A61B 5/00* (2006.01)

(52) U.S. Cl.
CPC .......... *A61B 5/6843* (2013.01); *A61B 5/6831* (2013.01); *A61B 2562/0247* (2013.01)

(58) Field of Classification Search
CPC ..... A61B 5/6843; A61B 5/6831; A61B 5/681; A61B 2562/0247
See application file for complete search history.

(56) References Cited

U.S. PATENT DOCUMENTS

| | | | | |
|---|---|---|---|---|
| 2004/0186387 A1* | 9/2004 | Kosuda | A61B 5/11 | |
| | | | 600/502 | |
| 2019/0082800 A1* | 3/2019 | Baranski | A44C 5/2071 | |
| 2021/0045687 A1* | 2/2021 | Wiese | A61B 5/14552 | |
| 2022/0401011 A1* | 12/2022 | Hyodo | A61B 5/4266 | |

* cited by examiner

*Primary Examiner* — Sana Sahand
(74) *Attorney, Agent, or Firm* — Barnes & Thornburg LLP

(57) ABSTRACT

A system includes a physiological measurement device, a pressure sensor, and a controller. The physiological measurement device includes a biosensor configured to measure physiological signals upon placement in contact with a user. The pressure sensor is configured to measure a surface contact pressure applied to the user by the biosensor. The controller is in communication with the pressure sensor or the biosensor (e.g. PPG or BioZ or other) or both.

19 Claims, 15 Drawing Sheets

INTEGRATED PRESSURE TRANSDUCER FOR PRECISE QUANTIFICATION OF APPLIED SURFACE FORCE IN WEARABLE DEVICES

CROSS-REFERENCE TO RELATED APPLICATIONS

This nonprovisional application claims the benefit and priority, under 35 U.S.C. § 119(e) and any other applicable laws or statutes, to U.S. Provisional Patent Application No. 63/437,421 filed on Jan. 6, 2023, the entire disclosure of which is hereby expressly incorporated herein by reference.

STATEMENT REGARDING FEDERALLY SPONSORED RESEARCH OR DEVELOPMENT

This invention was made with government support under Award Number 1648451 provided by NSF-ERC-PATHS-UP. The government has certain rights in the invention.

FIELD OF THE DISCLOSURE

The present disclosure relates generally to pressure transducers, and more specifically, to integrated pressure transducers for precise quantification of applied surface force in wearable devices.

BACKGROUND

Wearable biosensors are a key aspect in obtaining information from patients in the healthcare field. More recently, wearable biosensors have become more plentiful in consumer applications such as smart watches and exercise-related aspects. However, a number of undesirable noise and discrepancy sources can interfere with signal analysis from wearable biosensors placed on a skin surface of a user. In particular, variable pressures applied between the wearable biosensor and the skin can inhibit proper utilization.

Furthermore, during use of biosensors, measurable signals can change due to user movement, physiological variability with varying applied pressure, and probing different signal sources (i.e. blood volumes) due to variability in placement. As a result, biosignal morphology and time domain features can be drastically affected, causing variations in overall waveform shape, magnitude, and time between two signals.

SUMMARY

The present disclosure may comprise one or more of the following features and combinations thereof.

A system may comprise a physiological measurement device, a pressure sensor, and a controller. The physiological measurement device may include a biosensor, a strap, and a tensioner. The biosensor may be configured to measure physiological signals upon placement in contact with a user. The strap may be coupled to the biosensor. The tensioner may cooperate with the strap to fix a position of the biosensor relative to the user. The tensioner may be configured to adjust the strap to establish a surface contact pressure applied to the user by the biosensor when the biosensor is fixed in position relative to the user. The pressure sensor may be configured to measure the surface contact pressure applied to the user by the biosensor. The controller may be in communication with the pressure sensor. The controller may be configured to output an instruction associated with an optimized surface contact pressure to be implemented via the tensioner. The optimized surface contact pressure may be based, at least in part, on surface contact pressure data received from the pressure sensor so that the instruction can be used for alignment of the surface contact pressure data to the optimized surface contact pressure to manage a level of motion artifact in physiological signals measured by the biosensor thereby yielding improved physiological signal data output from the biosensor.

In some embodiments, the controller may be in communication with the biosensor. The instruction associated with the optimized surface contact pressure may be based, at least in part, on the physiological signal data from the biosensor. The controller may be in communication with a user interface. The controller may be configured to output the instruction associated with the optimized surface contact pressure to the user interface so that the user is informed of the optimized surface contact pressure to be implemented via the tensioner by the user. The instruction may be a visual indicator or an auditory indicator.

In some embodiments, the controller may be in communication with the tensioner. The controller may be configured to communicate the instruction associated with the optimized surface contact pressure to the tensioner. The tensioner may be configured to adjust the strap in response to receiving the instruction from the controller so that the surface contact pressure data aligns with the optimized surface contact pressure. The tensioner may be configured to provide infinitely variable adjustment of the strap. The controller may be configured to match the surface contact pressure data to the optimized surface contact pressure.

In some embodiments, the pressure sensor may be coupled to the strap and the biosensor may be coupled to the pressure sensor to locate the biosensor between the user and the pressure sensor. The pressure sensor may include one pressure transducer coupled to the biosensor to locate the biosensor between the user and the pressure transducer. A centerpoint of the pressure transducer may be aligned with a centerpoint of the biosensor.

In some embodiments, the tensioner may include a strap attachment body, a tensioner shaft, and a tensioning dial. The strap attachment body may be coupled to the strap to maintain a fixed position of the tensioner relative to the user. The tensioner shaft may be arranged to rotate about a fixed axis. The tensioning dial may be configured to be rotated to cause rotation of the tensioner shaft about the fixed axis. The strap may extend around the tensioner shaft so that rotation of the tensioning dial causes an effective length of the strap to decrease to adjust the surface contact pressure applied to the user by the biosensor.

In some embodiments, the tensioner may include a strap attachment body and an actuator. The strap attachment body may be coupled to the strap to maintain a fixed position of the tensioner relative to the user. The actuator may be configured to automatically decrease an effective length of the strap to adjust the surface contact pressure applied to the user by the biosensor.

According to another aspect of the present disclosure, a system may comprise a physiological measurement device, a pressure sensor, and a controller. The physiological measurement device may include a biosensor, a strap, and a tensioner. The biosensor may be configured to measure physiological signals. The strap may be coupled to the biosensor. The tensioner may cooperate with the strap to fix a position of the biosensor relative to the user. The tensioner may be configured to adjust the strap to establish a surface contact pressure applied to the user by the biosensor. The pressure sensor may be configured to measure the surface contact pressure applied to the user by the biosensor. The controller may be in communication with the pressure sensor. The controller may be configured to output an instruction associated with an optimized surface contact pressure to be implemented via the tensioner through adjustment of an effective length of the strap.

In some embodiments, the optimized surface contact pressure may be based, at least in part, on surface contact pressure data received from the pressure sensor. The controller may be in communication with the biosensor. The instruction associated with the optimized surface contact pressure may be based, at least in part, on the physiological signal data from the biosensor. The controller may be in communication with a user interface. The controller may be configured to output the instruction associated with the optimized surface contact pressure to the user interface so that the user is informed of the optimized surface contact pressure to be implemented via the tensioner by the user.

In some embodiments, the controller may be in communication with the tensioner. The controller may be configured to communicate the instruction associated with the optimized surface contact pressure to the tensioner. The tensioner may be configured to adjust the effective length of the strap in response to receiving the instruction from the controller so that the surface contact pressure data aligns with the optimized surface contact pressure.

A method of improving physiological signal data output from a biosensor may comprise providing a physiological measurement device, a pressure sensor, and a controller in communication with the pressure sensor. The physiological measurement device may include a biosensor configured to measure physiological signals, a strap coupled to the biosensor, and a tensioner. The method may comprise measuring a surface contact pressure applied to the user by the biosensor using the pressure sensor. The method may comprise storing surface contact pressure data in a memory of the controller. The method may comprise generating an instruction associated with an optimized surface contact pressure based, at least in part, on the surface contact pressure data received from the pressure sensor.

In some embodiments, the method may comprise outputting the instruction associated with the optimized surface contact pressure to a user interface. The method may comprise communicating the instruction associated with the optimized surface contact pressure to the tensioner and adjusting an effective length of the strap via the tensioner in response to receiving the instruction from the controller.

These and other features of the present disclosure will become more apparent from the following description of the illustrative embodiments.

DETAILED DESCRIPTION OF THE DRAWINGS

Figure 1:
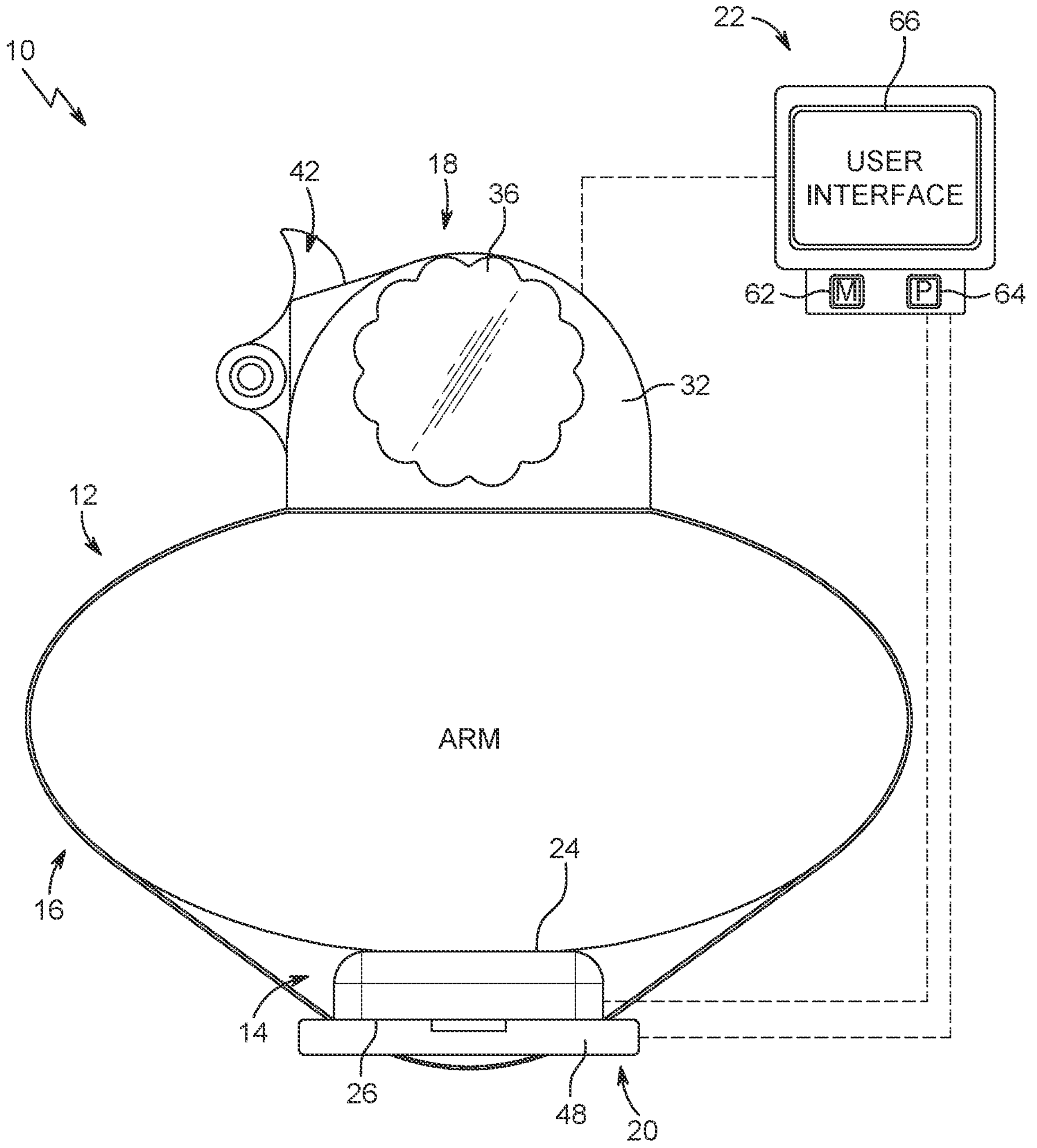
FIG. 1 is a perspective view of a system that includes a physiological measurement device configured to measure physiological signals of a user, a pressure sensor coupled to the physiological measurement device, and a controller, and further showing that the physiological measurement device includes a biosensor in contact with an arm of the user to measure the physiological signals, a strap that extends around the arm of the user, and a tensioner coupled to the strap to adjust a surface contact pressure applied to the user by the biosensor.

For the purposes of promoting an understanding of the principles of the disclosure, reference will now be made to a number of illustrative embodiments illustrated in the drawings and specific language will be used to describe the same.

The present disclosure provides a system including a wearable physiological measurement device and a pressure transducer or multiple pressure transducers to characterize biosignals with static and morphological features to provide biosignal analysis related to ailments and time-dependent physiological features, such as cuffless blood pressure. The systems of the present disclosure may be used for pressure transducer and controller integration on any wearable physiological measurement devices, thus providing a new dimension of biosignal analysis capable of a higher level of biomarker detection and cardiovascular feature extraction through control and maintenance of surface contact pressure based on the pressure transducer(s) signal or the biosensor signal from the device (e.g. PPG or BioZ or other) or both.

Figure 2:
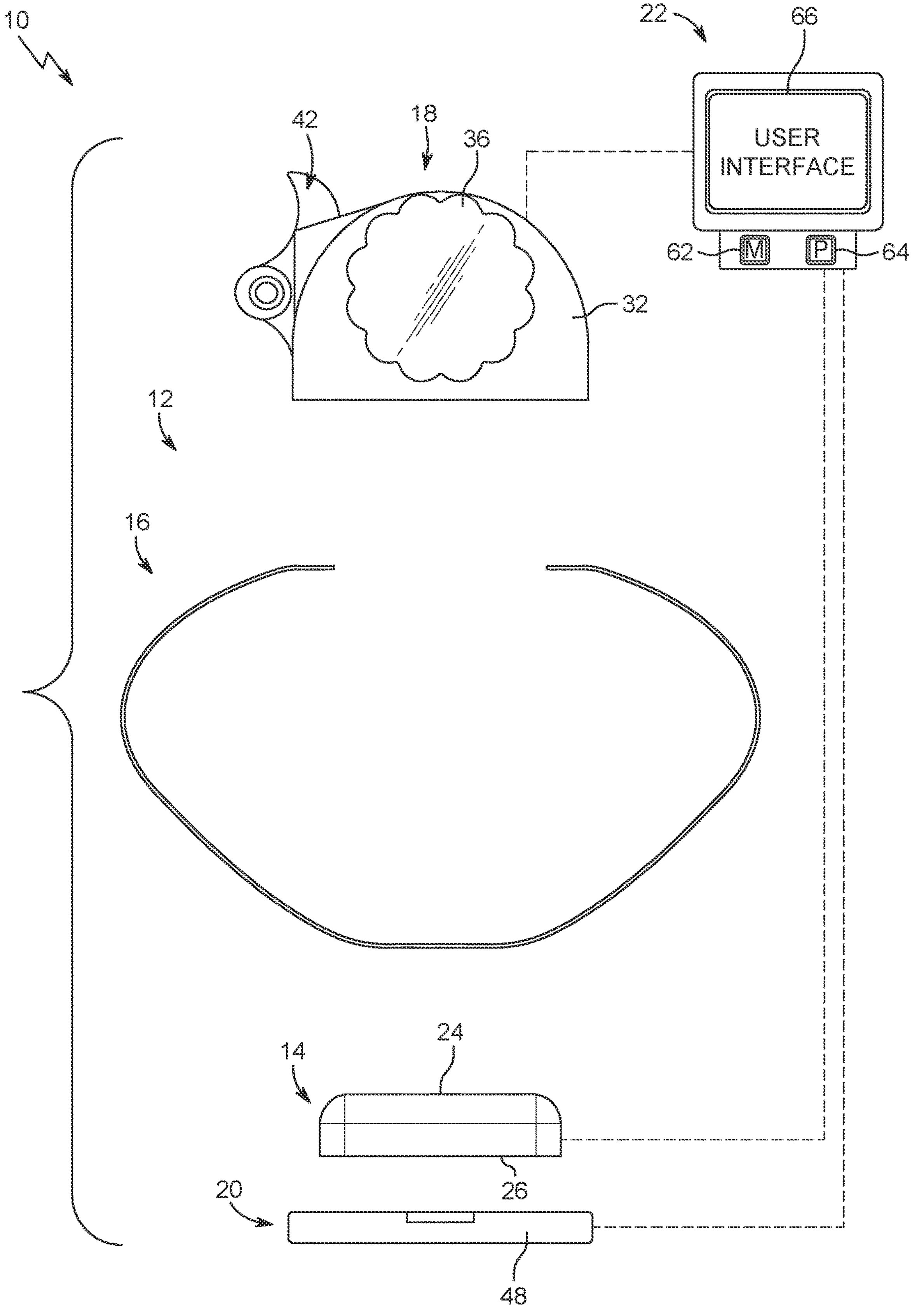
FIG. 2 is an exploded assembly view of the system of FIG. 1 showing that each of the pressure sensor, the biosensor, and the tensioner are in communication with the controller.
Figure 3:
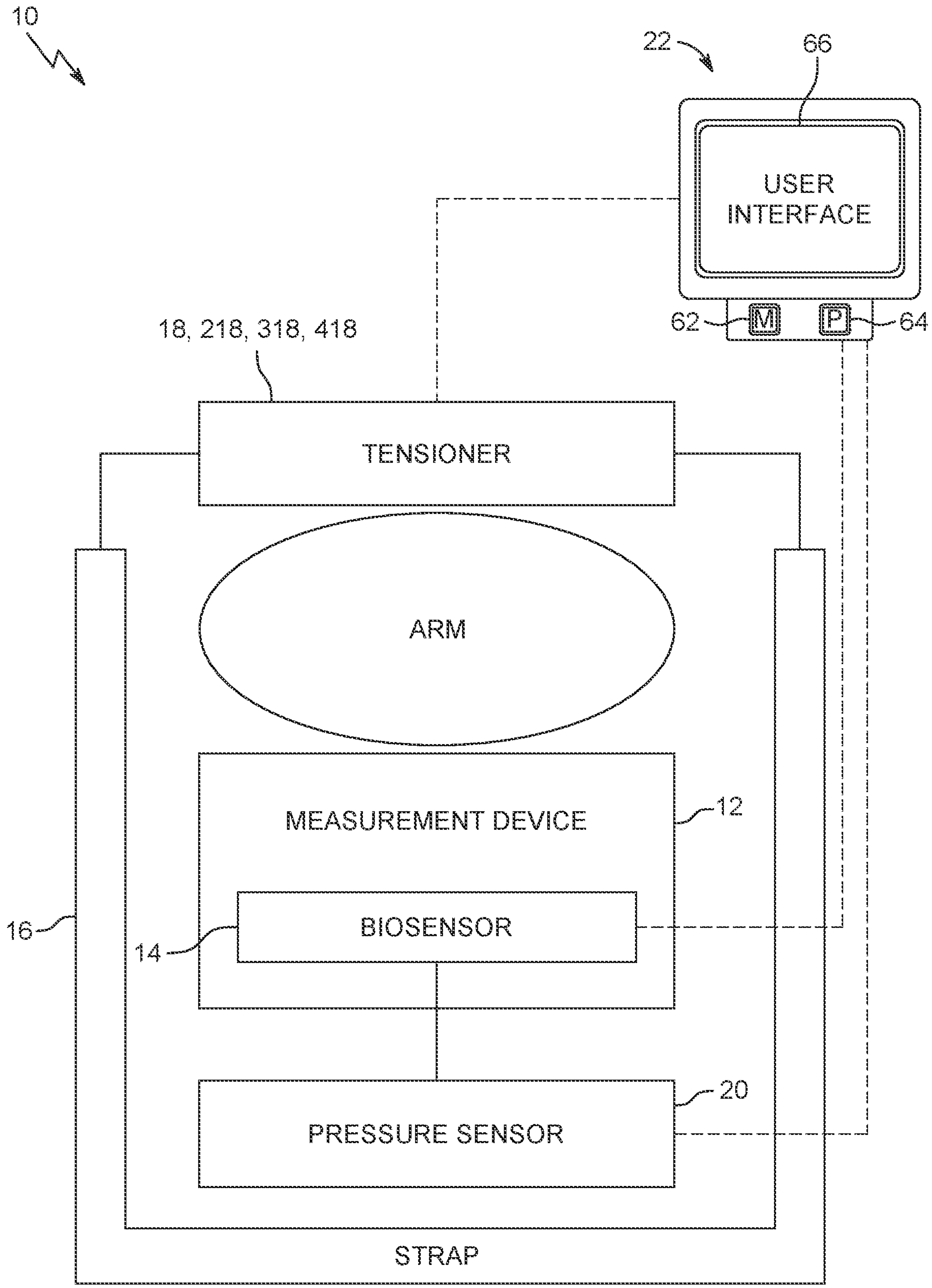
FIG. 3 is a block diagram of the system of FIG. 1 showing that the pressure sensor is coupled to the biosensor to locate the biosensor between the pressure sensor and the arm of the user.

A system 10 disclosed herein includes a physiological measurement device 12, a pressure sensor 20, and a controller 22 as shown in FIGS. 1-3. Illustratively, the physiological measurement device 12 is a wearable device that may be worn by a user. The physiological measurement device 12 includes a biosensor 14, a strap 16, and a tensioner 18 as shown in FIGS. 1-3. The biosensor 14 measures physiological signals of the user upon placement in contact with the user. The strap 16 is coupled to the biosensor 14 and is configured to extend around a portion of the user, for example, an arm or a wrist of the user. The tensioner 18 is coupled with the strap 16 and cooperates with the strap 16 to fix a position of the biosensor 14 relative to the user.

The pressure sensor 20 is coupled to the biosensor 14 of the physiological measurement device 12 as shown in FIG. 1. The pressure sensor 20 measures a surface contact pressure applied to the user by the biosensor 14. The controller 22 is in communication with the pressure sensor 20 as suggested in FIGS. 1-3.

Generally, during use of biosensors, physiological signals can change due to user movement, physiological variability with varying applied surface contact pressure, and probing different signal sources. As a result, biosignal morphology and time domain features can be drastically affected, causing variations in overall waveform shape, magnitude, and time between two signals. To minimize and/or manage a level of motion artifact in physiological signals, the system 10 allows for incremental surface contact pressure control to optimize the surface contact pressure applied to the user by the biosensor 14.

Establishing an optimized surface contact pressure between the biosensor 14 and the user yields improved physiological signal data output from the biosensor 14. The optimized surface contact pressure enhances and/or maximizes the biosensor 14 response. The pressure sensor 20 and the controller 22 cooperate to provide feedback regarding the surface contact pressure applied to the user by the biosensor 14 so that the surface contact pressure may be optimized.

Figure 4B:
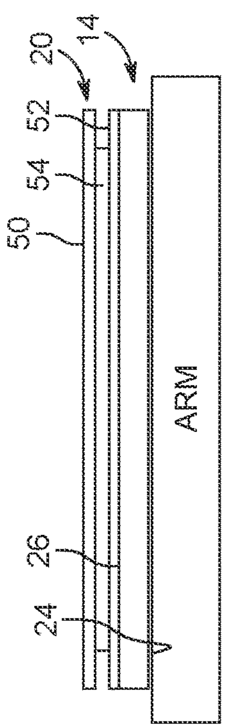
FIG. 4B is a side elevation view of the portion of the system of FIG. 4A showing that the photodiode and the light-emitting diode of the biosensor contact the arm of the user upon placement of the physiological measurement device on the user to locate the biosensor between the arm of the user and the pressure sensor.
Figure 4D:
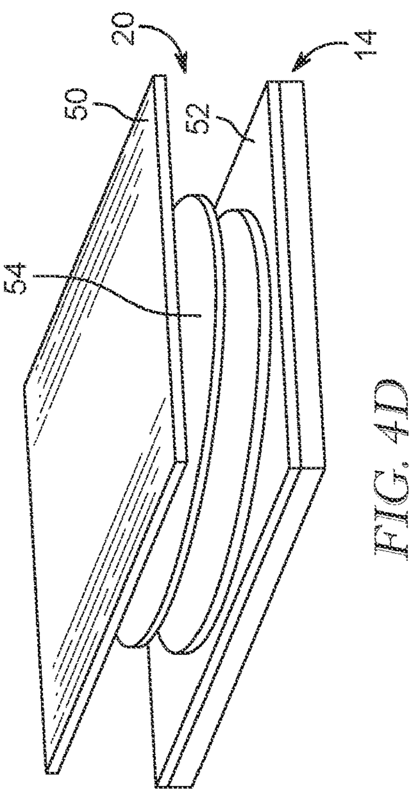
FIG. 4D is an exploded top perspective view of the portion of the system of FIG. 4A.
Figure 4A:
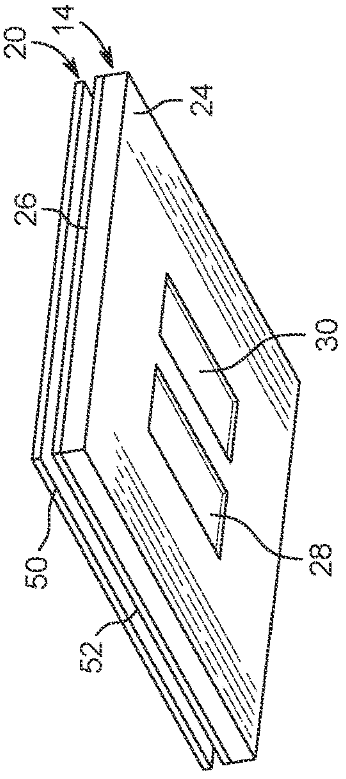
FIG. 4A is a perspective view of a portion of the system of FIG. 1 showing that the pressure sensor is coupled to the biosensor and the biosensor includes a photodiode and a light-emitting diode.
Figure 4C:
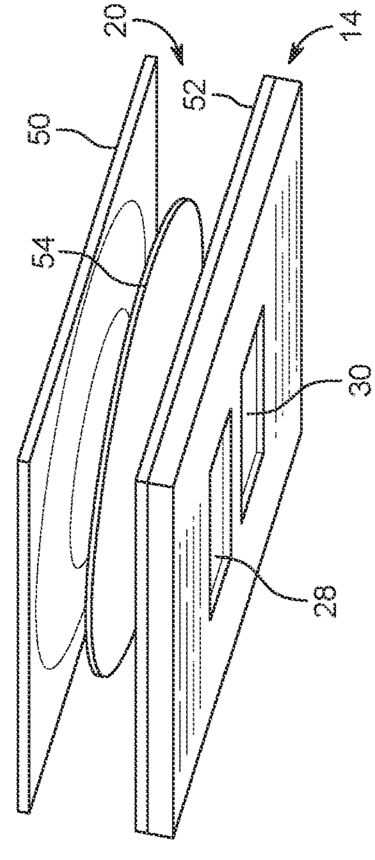
FIG. 4C is an exploded bottom perspective view of the portion of the system of FIG. 4A showing that the pressure sensor includes a first receiver plate, a second receiver plate coupled to the biosensor, and a pressure transducer arranged between the first receiver plate and the second receiver plate.

Turning back to the physiological measurement device 12, the biosensor 14 contacts the user, such as the wrist or the arm of the user, to measure physiological signals as shown in FIG. 1. A first side 24 of the biosensor 14 contacts the user, and a second side 26 of the biosensor 14 opposite the first side 24 is coupled to the pressure sensor 20 as shown in FIGS. 1 and 4B. In some embodiments, the biosensor 14 includes a photodiode 28 and/or an LED 30 as shown in FIGS. 4A and 4C.

The biosensor 14 may include a bioimpedance sensor (BioZ), a photoplethysmogram sensor (PPG), a micro-electro-mechanical system (MEMS) sensor, or any other suitable sensor or combination thereof. The physiological signals measured by the biosensor 14 include heart rate (HR), heart rate variability (HRV), blood pressure (BP), and any other physiological signals.

The strap 16 of the physiological measurement device 12 couples the biosensor 14 to the user as shown in FIG. 1. For example, the strap 16 may extend around the wrist of the user so that the biosensor 14 remains in contact with the wrist of the user. The strap 16 has a predefined length as suggested in FIG. 2. The strap 16 has an effective length, which is defined as a length of the portion of the strap 16 that extends around the wrist of the user. The effective length may be equal to the predefined total length of the strap 16 or less than the predefined total length.

The strap 16 may be tightened on the wrist of the user to decrease the effective length and increase the surface contact pressure applied to the user by the biosensor 14. The strap 16 may be loosened on the wrist of the user to increase the effective length and decrease the surface contact pressure applied to the user by the biosensor 14. Illustratively, the tightening and loosening of the strap 16 around the wrist of the user adjusts the effective length of the strap 16.

In some embodiments, the strap 16 extends through a portion of the pressure sensor 20 to couple the pressure sensor 20 (and the biosensor 14) thereto as shown in FIG. 1. In some embodiments, the strap 16 extends through a portion of the biosensor 14 to couple the biosensor 14 (and the pressure sensor 20) thereto.

The tensioner 18 of the physiological measurement device 12 adjusts the effective length of the strap 16 to establish the surface contact pressure applied to the user by the biosensor 14 when the biosensor 14 is fixed in position relative to the user as suggested in FIG. 1. Illustratively, the tensioner 18 increases or decreases the effective length of the strap 16 to tighten or loosen the strap 16 on the user, which adjusts the surface contact pressure applied to the user.

Figure 11:
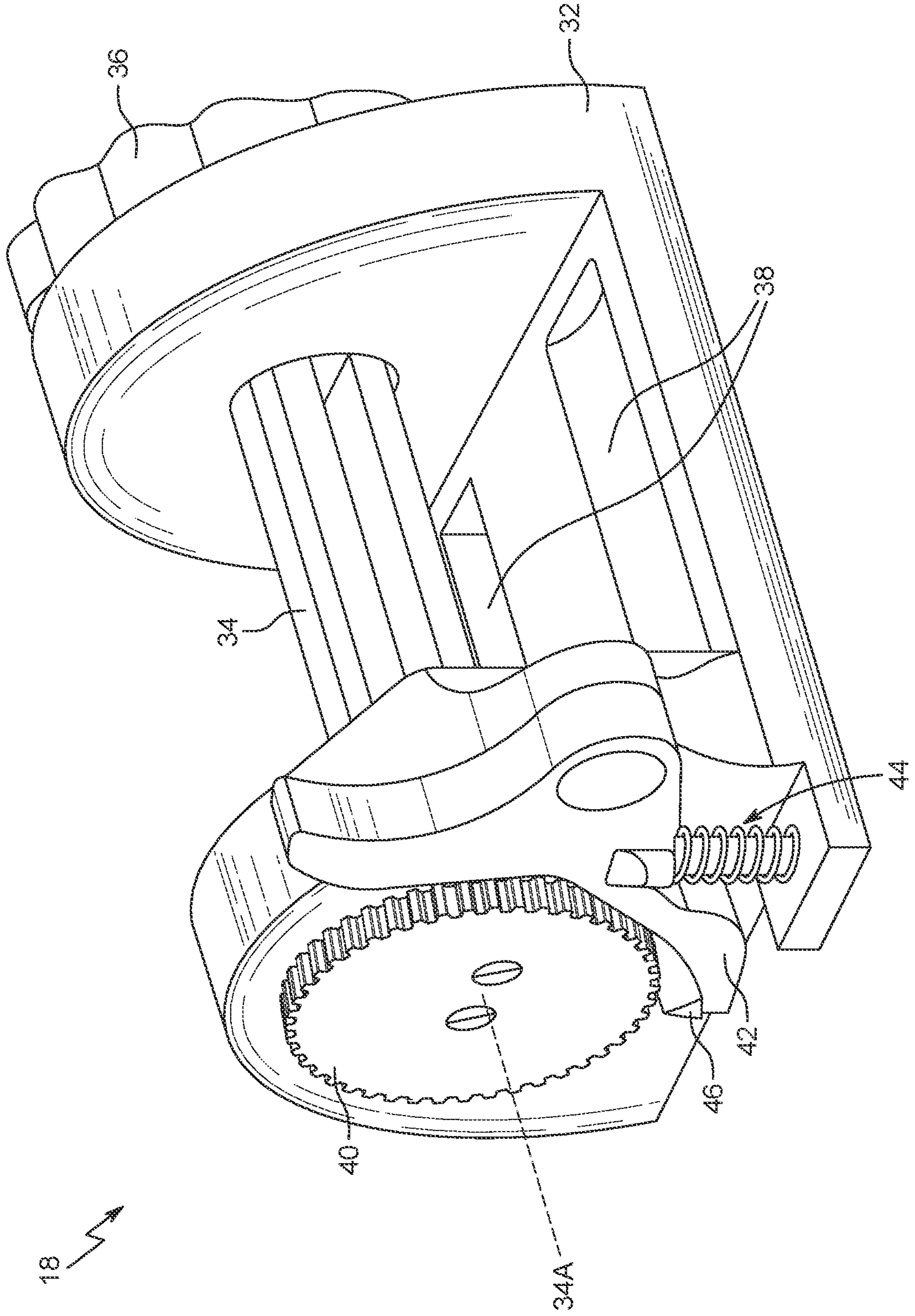
FIG. 11 is a perspective view of the tensioner of FIG. 1 showing that the tensioner includes a strap attachment body configured to be removably coupled to the strap to maintain a fixed position of the tensioner relative to the arm of the user, a tensioner shaft arranged to rotate about a fixed axis, and a tensioning dial configured to be rotated by the user to cause rotation of the tensioner shaft so that the strap wraps around the tensioner shaft to tighten the strap on the arm of the user to adjust the surface contact pressure applied to the user by the biosensor.

In some embodiments, as shown in FIGS. 1 and 11, the tensioner 18 includes a strap attachment body 32, a tensioner shaft 34, and a tensioning dial 36. The strap attachment body 32 is coupled to the strap 16, as shown in FIG. 1, to maintain a fixed position of the tensioner 18 relative to the user. The strap 16 extends through strap attachment channels 38 formed in the strap attachment body 32 to attach the tensioner 18 to the strap 16. The tensioner shaft 34 is configured to rotate about a fixed axis 34A as the tensioning dial 36 rotates about the fixed axis 34A. A portion of the strap 16 extends and/or wraps around the tensioner shaft 34 so that the rotation of the tensioner shaft 34 tightens the strap 16 around the arm of the user. Rotation of the tensioning dial 36 causes rotation of the tensioner shaft 34, which causes the strap 16 to wind around the tensioner shaft 34.

Illustratively, rotation of the tensioning dial 36 adjusts the effective length of the strap 16 so that the surface contact pressure applied to the user by the biosensor 14 is adjusted accordingly. In some embodiments, the user rotates the tensioning dial 36 to adjust the effective length of the strap 16.

The tensioner 18 further includes a ratchet spur 40, a lock arm 42, and a biasing member 44 as shown in FIG. 11. The ratchet spur 40 rotates with the tensioner shaft 34 about the fixed axis 34A. The lock arm 42 is formed to include a protrusion 46 that engages teeth of the ratchet spur 40. The lock arm 42 is configured to pivot about a lock arm axis between an engaged position, in which the protrusion 46 of the lock arm 42 engages the ratchet spur 40 to block rotation of the tensioning dial 36, and a disengaged position, in which the protrusion 46 moves away from the ratchet spur 40 so that the tensioning dial 36 is free for rotation. The biasing member 44 urges the lock arm 42 to the engaged position so that the protrusion 46 engages the teeth of the ratchet spur 40.

When the physiological measurement device 12 is attached to the user, the biosensor 14 to located between the user, such as the arm or the wrist of the user, and the pressure sensor 20 as shown in FIG. 1. In some embodiments, the tensioner 18 and the biosensor 14 are located on opposing sides of the strap 16 such that the tensioner 18 is located on one side of the arm or the wrist and the biosensor 14 is located on the opposite side of the arm or the wrist as shown in FIG. 1. The arm or the wrist is located between the tensioner 18 and the biosensor 14, and the arm or the wrist is located between the tensioner 18 and the pressure sensor 20. In such an embodiment, the tensioner 18 is separate from the biosensor 14 and the pressure sensor 20 as shown in FIG. 1.

Figure 15:
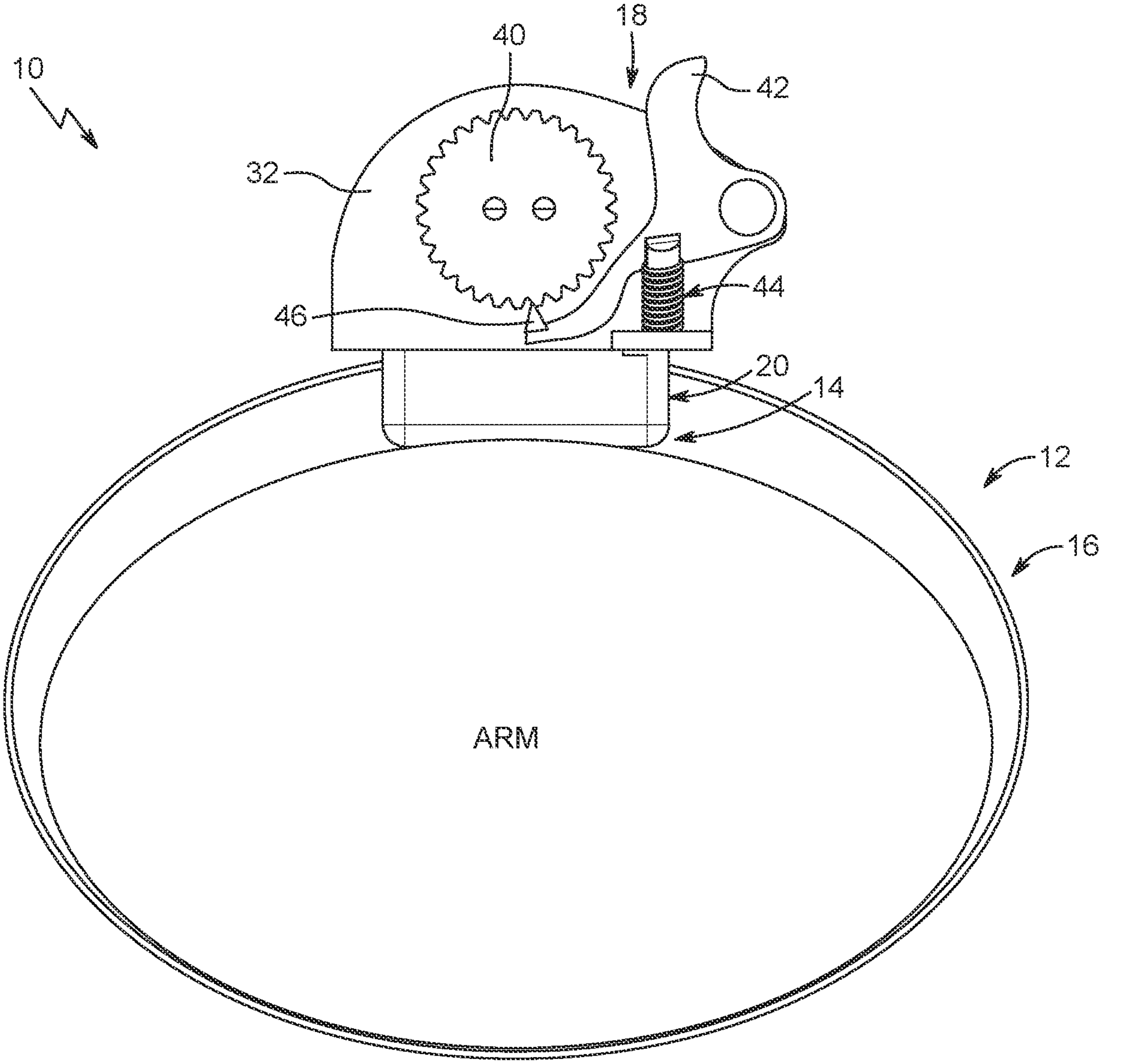
FIG. 15 is an alternative embodiment of a system in which a tensioner, a biosensor, and a pressure sensor are integrated with one another so that the pressure sensor is arranged between the tensioner and the biosensor.

In alternative embodiments, the tensioner 18 is integrated with the biosensor 14 and the pressure sensor 20 as shown in FIG. 15. In such an embodiment, the pressure sensor 20 is arranged between the tensioner 18 and the biosensor 14.

In some embodiments, the tensioner 18 is omitted and the tensioner instead comprises a hook-and-loop fastener. In such an embodiment, the effective length of the strap 16 is adjusted by altering the location of attachment of the hook-and-loop fastener. In some embodiments, the tensioner 18 is omitted and the tensioner instead comprises holes extending through a first end of the strap 16 and a tab coupled to a second end of the strap 16 and configured to extend through the holes. In such an embodiment, the effective length of the strap 16 is adjusted by changing the hole through which the tab extends.

The pressure sensor 20 is coupled to each of the strap 16 and the biosensor 14 as shown in FIG. 1. The pressure sensor 20 measures the surface contact pressure applied to the user by the biosensor 14.

The pressure sensor 20 includes a housing 48, a first receiver plate 50, a second receiver plate 52, and a pressure transducer 54 as shown in FIGS. 1, 4A, 4B, 4C, and 4D. The housing 48 is formed around the receiver plates 50, 52 and the pressure transducer 54. In some embodiments, the strap 16 extends through the housing 48 to couple the pressure sensor 20 to the strap 16. The pressure transducer 54 is located between the first receiver plate 50 and the second receiver plate 52 as shown in FIG. 4B.

Figure 5:
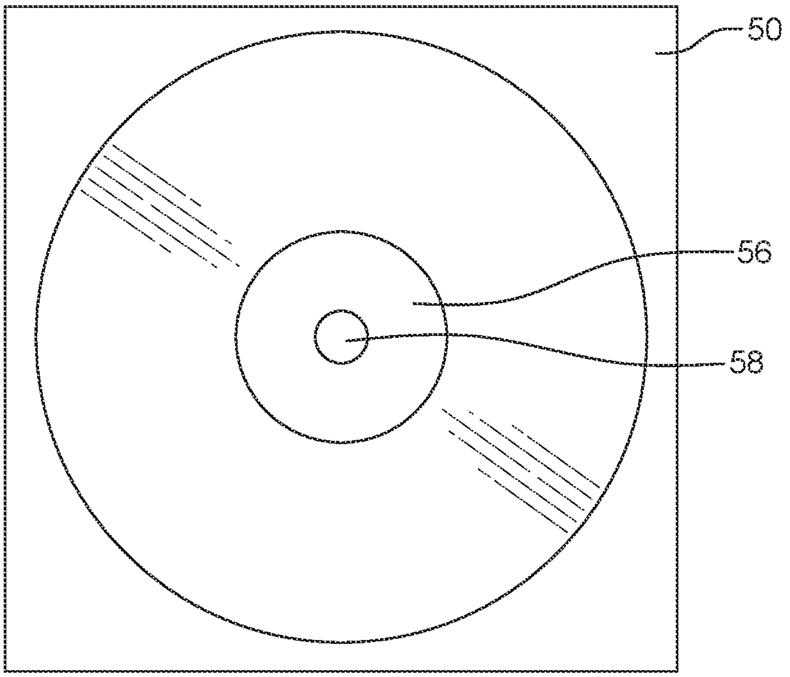
FIG. 5 is a top view of a portion of the pressure sensor of FIG. 4A showing that the pressure sensor is formed to include a pressure transducer cup and a pressure transducer interface configured to contact the pressure transducer shown in FIG. 6.
Figure 6:
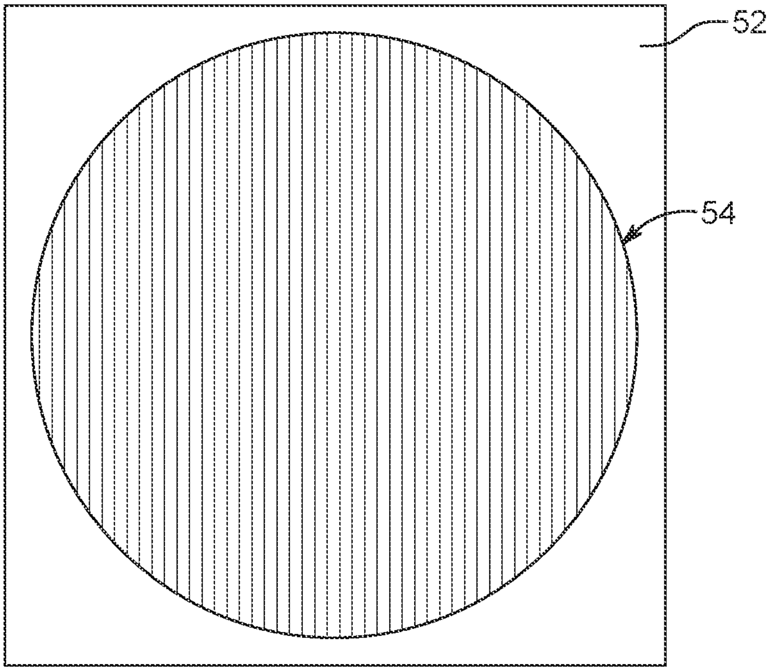
FIG. 6 is a top view of a portion of the pressure sensor of FIG. 4A showing the pressure sensor includes one pressure transducer and the pressure transducer has a round shape.

In some embodiments, the pressure sensor 20 includes a pressure transducer cup 56 and a pressure transducer interface 58 as shown in FIG. 5. The pressure transducer interface 58 is arranged in the pressure transducer cup 56 to contact the pressure transducer 54. A centerpoint of the pressure transducer interface 58 is aligned with a centerpoint of the pressure transducer 54 when the pressure sensor 20 components are stacked together as suggested in FIGS. 5 and 6. The pressure transducer interface 58 may be varied in height, radius, and/or width to allow for direct tuning of the pressure transducer 54. Direct tuning of the pressure transducer 54 via the pressure transducer interface 58 may increase the performance of the pressure transducer 54 in desired pressure ranges.

Figure 7:
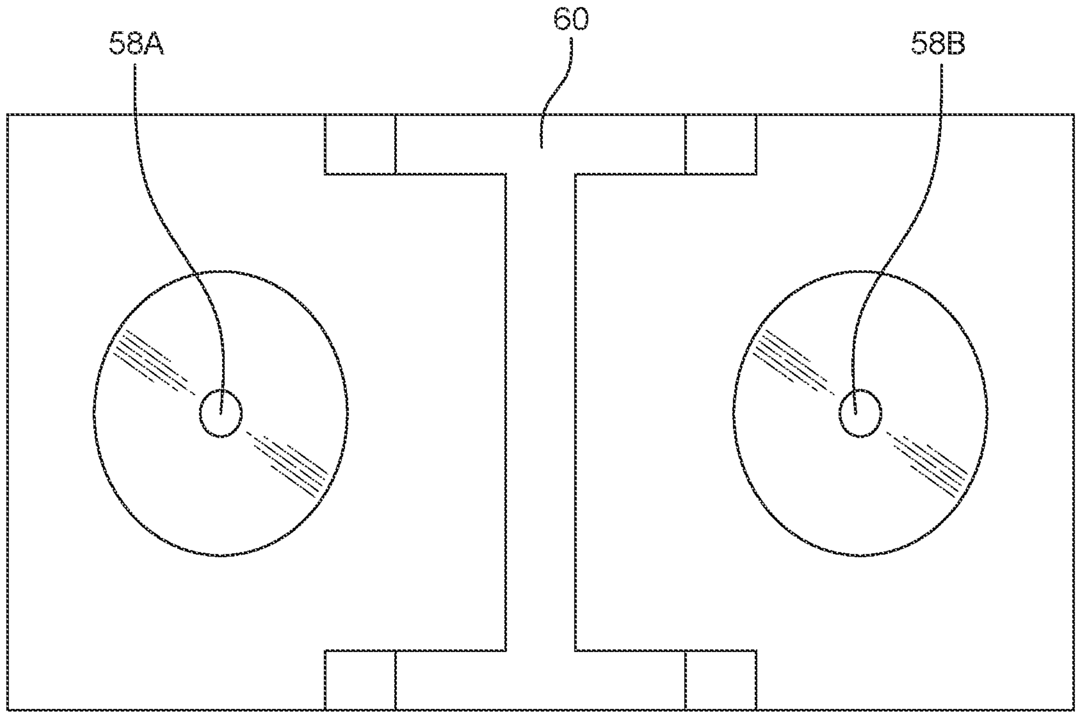
FIG. 7 is a top view of another embodiment of a pressure sensor for use with the system of FIG. 1 showing that the pressure sensor includes two pressure transducer interfaces configured to contact two pressure transducers.
Figure 8:
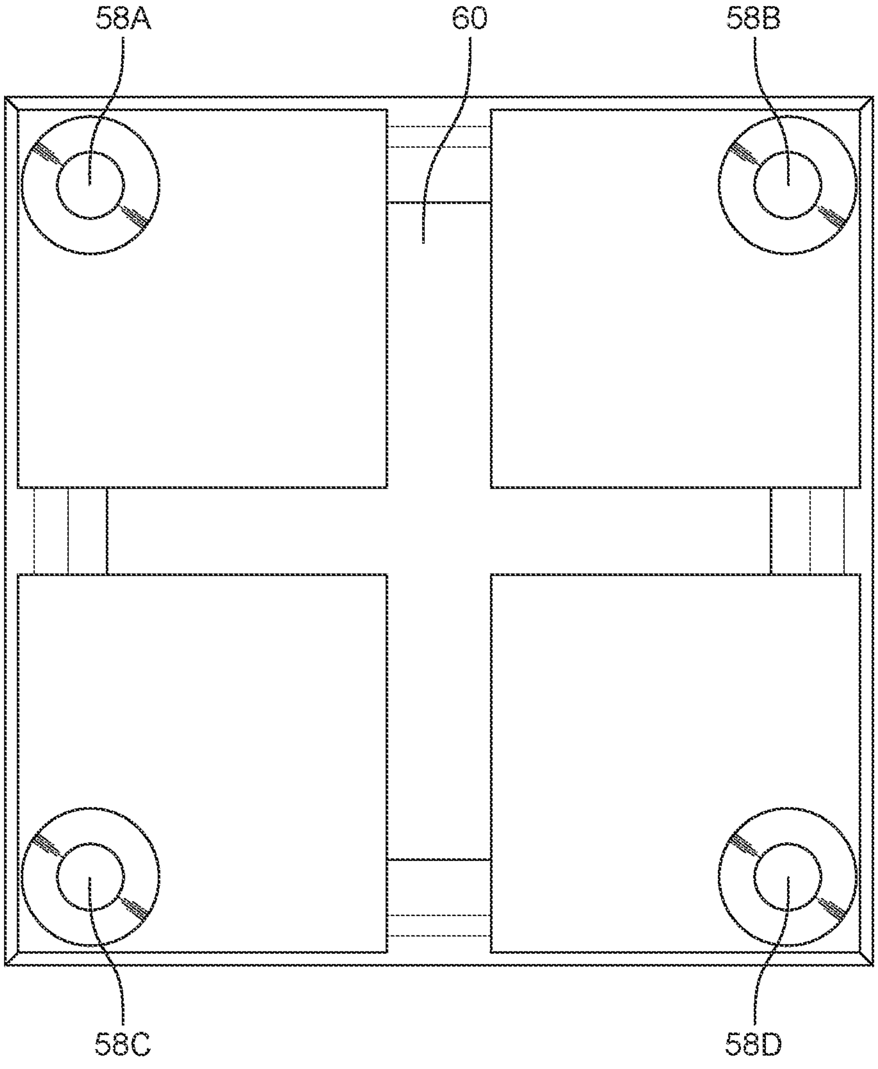
FIG. 8 is a top view of another embodiment of a pressure sensor for use with the system of FIG. 1 showing that the pressure sensor includes four pressure transducer interfaces configured to contact four pressure transducers.
Figure 9A:
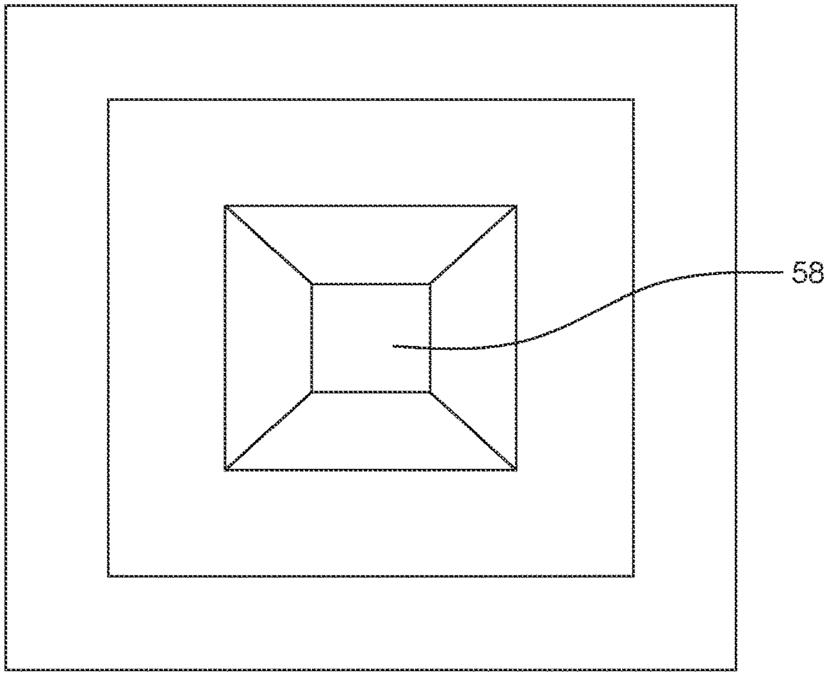
FIG. 9A is a top view of another embodiment of a pressure sensor for use with the system of FIG. 1 showing that the pressure sensor includes one pressure transducer interface configured to contact one pressure transducer and the pressure transducer interface has a square shape.
Figure 9B:
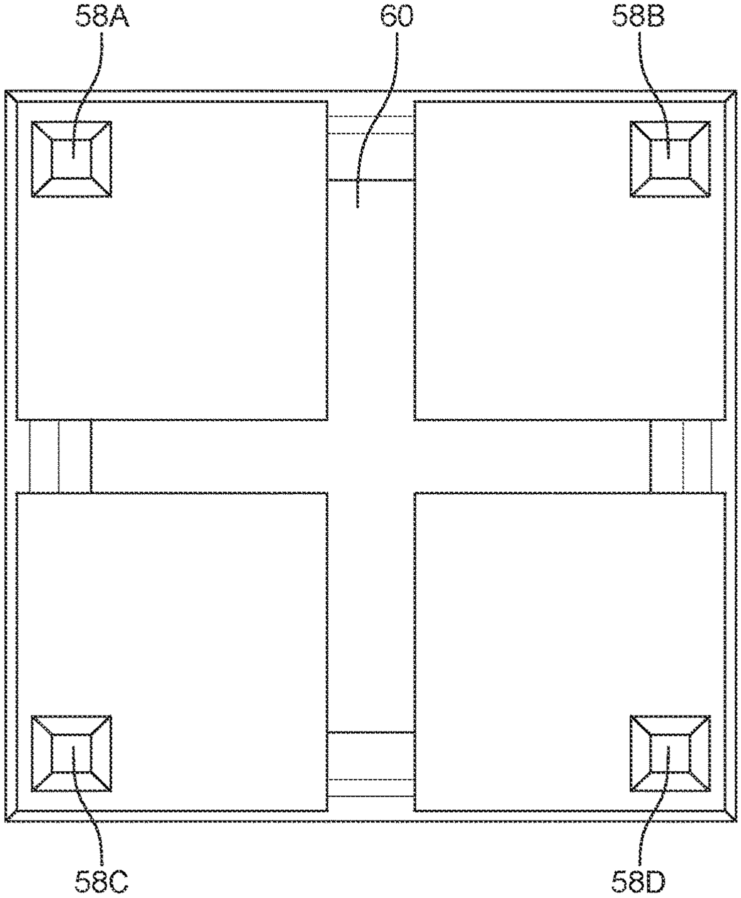
FIG. 9B is a top view of another embodiment of a pressure sensor for use with the system of FIG. 1 showing that the pressure sensor includes four pressure transducer interfaces configured to contact four pressure transducers and the pressure transducer interfaces each have a square shape.
Figure 10A:
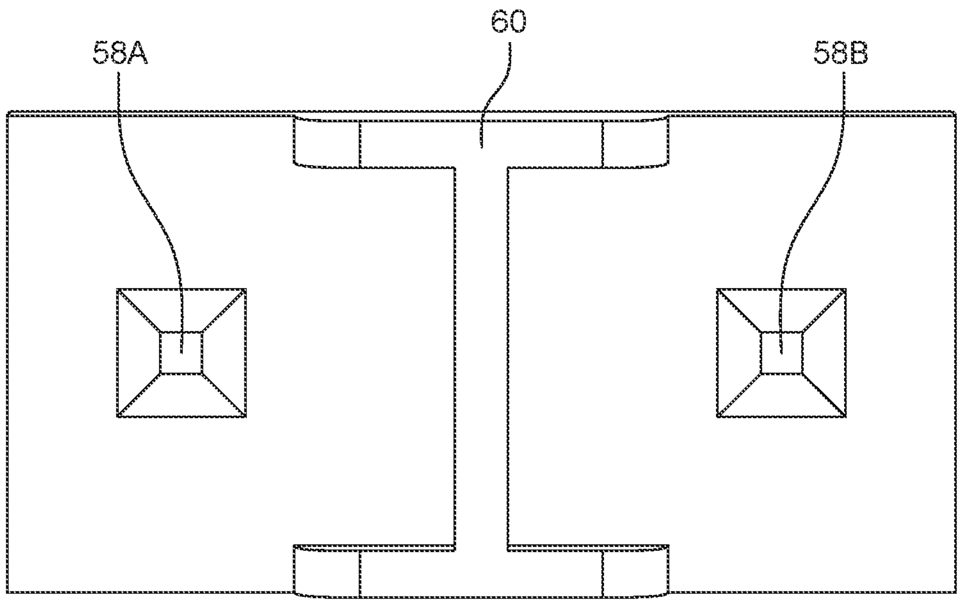
FIG. 10A is a top view of another embodiment of a pressure sensor for use with the system of FIG. 1 showing that the pressure sensor includes two pressure transducer interfaces configured to contact two pressure transducers shown in FIG. 10B and the pressure transducer interfaces each have a square shape.
Figure 10B:
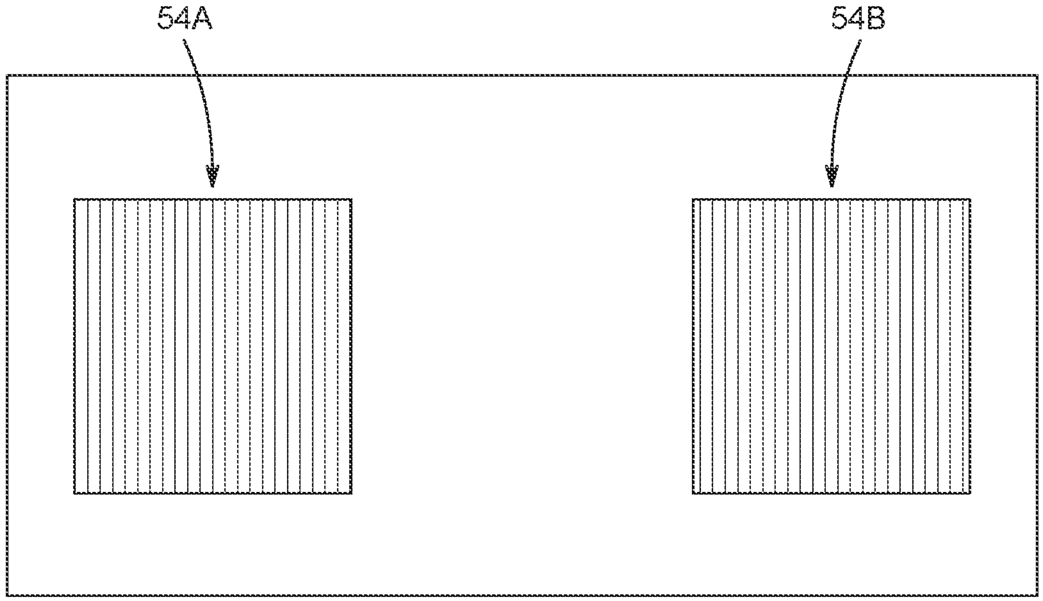
FIG. 10B is a top view of the two pressure transducers configured to contact the two pressure transducer interfaces of FIG. 10A showing that each of the two pressure transducers have a square shape.

In some embodiments, the pressure sensor 20 includes one pressure transducer 54 as shown in FIGS. 4A-6. A centerpoint of the pressure transducer 54 is aligned with a centerpoint of the biosensor 14 as shown in FIG. 4D. In some embodiments, the pressure sensor 20 includes at least one tension rib 60 as shown in FIGS. 7 and 8. At least one tension rib 60 may be adjusted in height and thickness to vary the flexibility and/or compliance of the pressure sensor 20. At least one tension rib 60 allows the pressure transducer 54 to be tuned to specific surface contact pressure ranges.

In some embodiments, the pressure sensor 20 includes two pressure transducers and two pressure transducer interfaces 58A, 58B as shown in FIG. 7. One of the two pressure transducers and one of the two pressure transducer interfaces 58A is arranged on a first half of the pressure sensor 20 and the other of the two pressure transducers and other of the two pressure transducer interfaces 58B is arranged on a second half of the pressure sensor 20. A centerpoint of one of the two pressure transducers is aligned with a centerpoint of one of the two pressure transducer interfaces 58A, and a centerpoint of the other of the two pressure transducers is aligned with a centerpoint of the other of the two pressure transducer interfaces 58B.

In some embodiments, the pressure sensor 20 includes four pressure transducers and four pressure transducer interfaces 58A, 58B, 58C, 58D as shown in FIG. 8. One pressure transducer and one pressure transducer interface is located in each of four equally sized quadrants of the pressure sensor 20.

In some embodiments, the pressure transducer(s) 54 and the pressure transducer interface(s) 58 have a round shape as shown in FIGS. 4C-8. In some embodiments, the pressure transducer(s) 54 and the pressure transducer interface(s) 58 have a square shape as shown in FIGS. 9A-10B. Though shown and described as having a round shape or a square shape, the pressure transducer(s) 54 and the pressure transducer interface(s) 58 may have any suitable shape.

In some embodiments, the pressure transducer(s) 54 are piezoelectric transducers. In some embodiments, the pressure transducer(s) 54 are ceramic transducers. In some embodiments, the pressure transducer(s) 54 are strain gauge-based transducers. In some embodiments, the pressure transducer(s) 54 are a combination of piezoelectric transducers, ceramic transducers, and/or strain-gauge based transducers. For example, the pressure transducer(s) 54 may comprise a combination of piezoelectric transducers and ceramic transducers. Dual material elements for the pressure transducer(s) 54 may increase sensitivity of the pressure transducer(s) 54 while maintaining a dynamic range.

In some embodiments, the pressure sensor 20 is separate from the biosensor 14. In some embodiments, the pressure sensor 20 is integrated with the biosensor 14.

The controller 22 is in communication with the pressure sensor 20 to receive surface contact pressure data therefrom as suggested in FIGS. 1-3. The controller 22 stores the surface contact pressure data in a memory 62 of the controller 22. The controller 22 outputs an instruction associated with an optimized surface contact pressure to be implemented by the tensioner 18. The instruction is based, at least in part, on the surface contact pressure data received from the pressure sensor 20. A processor 64 of the controller 22 may compare the surface pressure contact data with the optimized surface contact pressure to determine the instruction. For example, the surface contact pressure data may indicate that the surface contact pressure applied to the user by the biosensor 14 is less (or more) than the optimized surface contact pressure for improved physiological signal data output from the biosensor 14.

The instruction associated with the optimized surface contact pressure may be used for alignment of the surface contact pressure data to the optimized surface contact pressure. For example, if the surface contact pressure data indicates that the surface contact pressure applied to the user by the biosensor 14 is less than desirable, the instruction may indicate that the surface contact pressure should be increased so that the surface contact pressure data aligns with the optimized surface contact pressure. To align the surface contact pressure data with the optimized surface contact pressure, the strap 16 is tightened (i.e., the effective length of the strap 16 is decreased) via the tensioner 18.

In some embodiments, the controller 22 is in communication with the biosensor 14 so that the physiological signal data output from the biosensor 14 is transmitted to the controller 22 and stored in the memory 62 of the controller 22. The instruction associated with the optimized surface contact pressure may also be based, at least in part, on the physiological signal data from the biosensor 14. For example, the processor 64 may analyze the physiological signal data to determine a level of noise in the data. If the level of noise is greater than a threshold, the instruction may indicate that the surface contact pressure should be adjusted to decrease the level of noise.

In some embodiments, the controller 22 is in communication with and/or comprises a user interface 66 as shown in FIG. 1. The controller 22 is configured to output the instruction associated with the optimized surface contact pressure to the user interface 66 so that the user is informed of the instruction associated with the optimized surface contact pressure. In some embodiments, the instruction may comprise a visual indicator. For example, the visual indicator may include a color, a phrase, an image, or a combination of the same. In some embodiments, the instruction may comprise an auditory indicator. Based on the instruction, the user may adjust the effective length of the strap 16 via the tensioner 18.

As one example, if the user interface 66 depicts a visual indicator, such as a red light, the user is informed that the surface contact pressure data is not aligned with the optimized surface contact pressure. Then, the user may rotate the tensioning dial 36 to tighten the strap 16 and decrease the effective length of the strap 16, thereby aligning the surface contact pressure data with the optimized surface contact pressure.

In some embodiments, the controller 22 is separate from the biosensor 14 and the pressure sensor 20 as shown in FIG. 1. In some embodiments, the controller 22 is integrated with the biosensor 14. In some embodiments, the controller 22 is integrated with the pressure sensor 20.

Alternative embodiments of a tensioner 218, 318, 418 in accordance with the present disclosure are shown in FIGS. 12A-14B. The tensioners 218, 318, 418 are substantially similar to the tensioner 18 shown in FIGS. 1-3 and 11 and described herein.

In some embodiments, the controller 22 is in communication with the tensioner 218, 318, 418 to provide for automatic adjustment of the strap 16 via the tensioner 218, 318, 418 without user involvement. The controller 22 is configured to communicate the instruction associated with the optimized surface contact pressure to the tensioner 218, 318, 418. Based on the instruction, the tensioner 218, 318, 418 tightens the strap 16 (i.e., decreases the effective length of the strap 16). The tensioner 218, 318, 418 is configured to provide infinitely variable adjustment of the strap 16 so that the surface contact pressure data matches the optimized surface contact pressure.

Figure 12A:
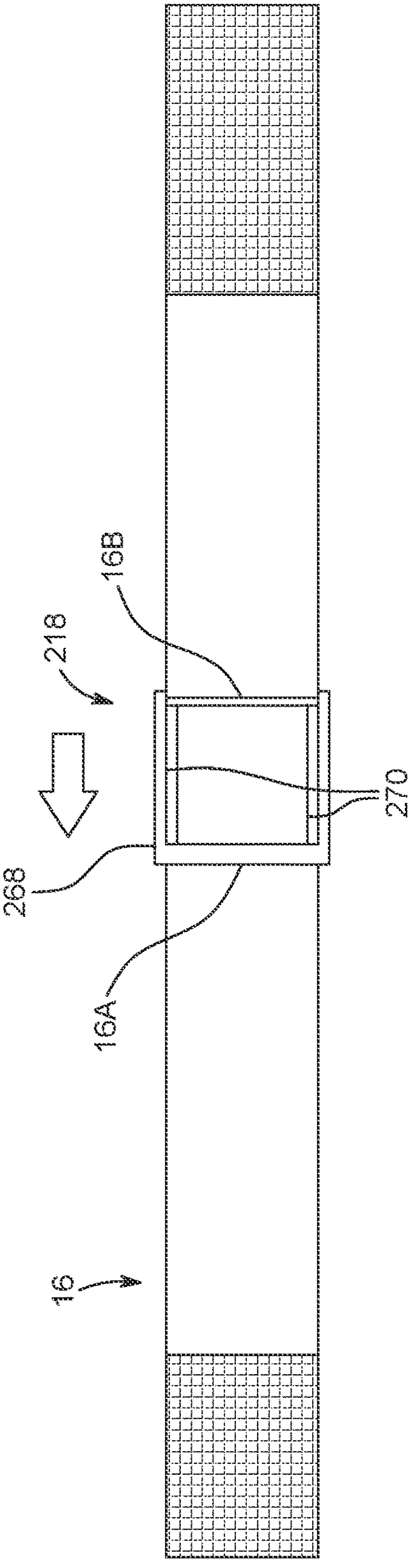
FIG. 12A is a top view of another embodiment of a tensioner for use with the system of FIG. 1 showing that the tensioner includes a strap attachment body configured to be coupled to the strap to maintain a fixed position of the tensioner relative to the arm of the user and an actuator configured to move a second end of the strap toward a first end of the strap to tighten the strap on the arm of the user to adjust the surface contact pressure applied to the user by the biosensor.
Figure 12B:
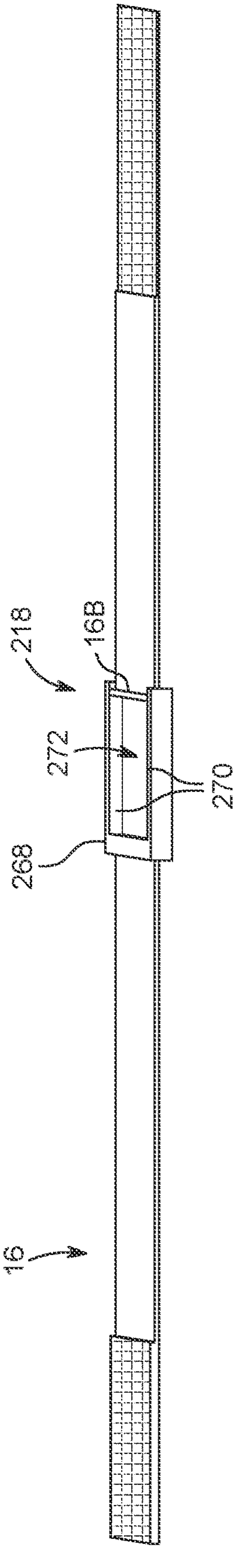
FIG. 12B is a perspective view of the tensioner of FIG. 12A showing that the first end and the second end of the strap are spaced apart from one another so that the actuator can move the second end of the strap toward the first end of the strap to tighten the strap on the arm of the user.

The tensioner 218 includes a strap attachment body 268 and an actuator 270 as shown in FIGS. 12A and 12B. A first end 16A of the strap 16 is coupled to the strap attachment body 268 in a fixed position, and a second end 16B of the strap 16 opposite the first end 16A is coupled to the strap attachment body 268 for movement relative to the strap attachment body 268. The strap attachment body 268 is formed to include a recess 272 to receive the second end 16B of the strap 16 as the second end 16B of the strap 16 slides in the recess 272 and toward the first end 16A of the strap 16. In response to the instruction, the actuator 270 drives horizontal movement of the second end 16B of the strap 16 toward the first end 16A of the strap 16 to decrease the effective length of the strap 16 so that the surface contact pressure data aligns with and/or matches the optimized surface contact pressure.

Figure 13A:
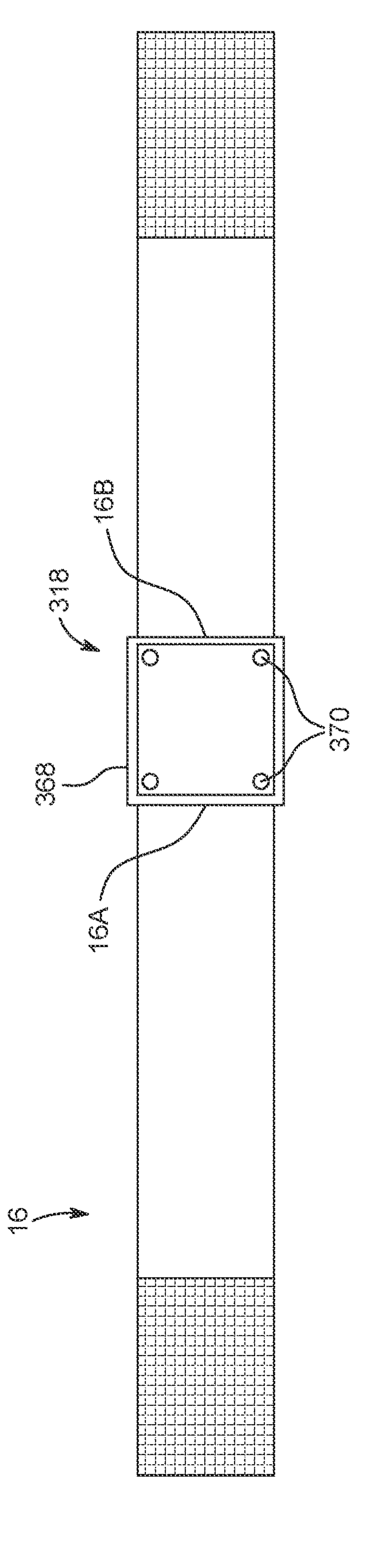
FIG. 13A is a top view of another embodiment of a tensioner for use with the system of FIG. 1 showing that the tensioner includes a strap attachment body configured to be coupled to the strap to maintain a fixed position of the tensioner relative to the arm of the user and an actuator configured to move each of the first end and the second end of the strap in a vertical direction to tighten the strap on the arm of the user to adjust the surface contact pressure applied to the user by the biosensor.
Figure 13B:
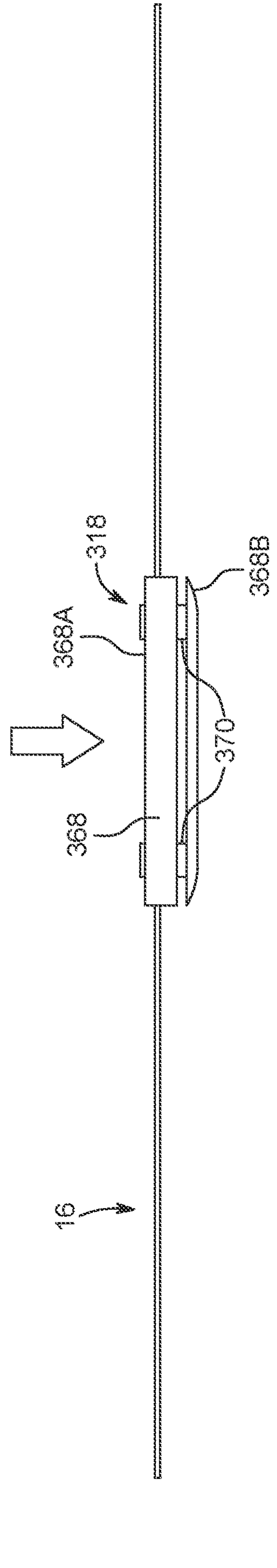
FIG. 13B is a side view of the tensioner of FIG. 13A showing that the strap attachment body includes a first plate and a second plate spaced apart from the first plate, and further suggesting that the actuator is configured to move the second plate away from the first plate to move the first end and the second end of the strap in the vertical direction to tighten the strap on the arm of the user.

As shown in FIGS. 13A and 13B, the tensioner 318 includes a strap attachment body 368 and an actuator 370. The first end 16A and the second end 16B of the strap 16 are each coupled to the strap attachment body 368. The strap attachment body 368 includes a first plate 368A and a second plate 368B spaced apart from the first plate 368A. The actuator 370 is configured to move the second plate 368B away from the first plate 368A to move the first end 16A and/or the second end 16B of the strap 16 in the vertical direction. In response to the instruction, the actuator 370 drives vertical movement of the first end 16A and/or the second end 16B of the strap 16 to decrease the effective length of the strap 16 so that the surface contact pressure data aligns with and/or matches the optimized surface contact pressure.

Figure 14A:
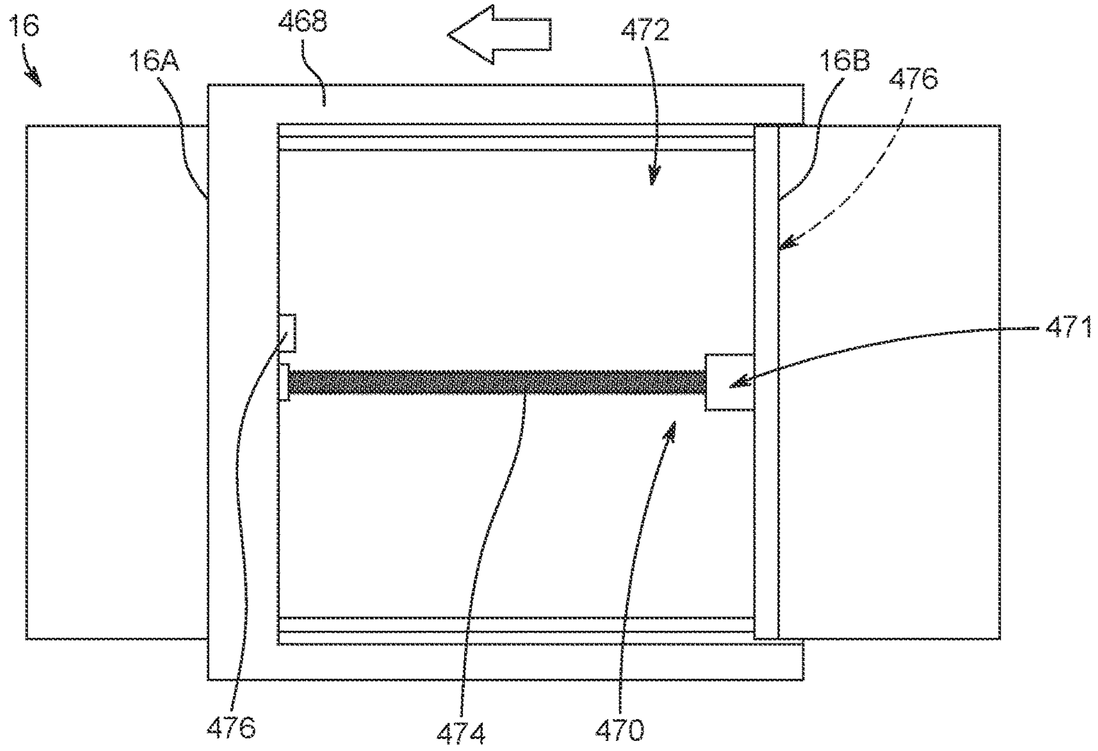
FIG. 14A is a top view of another embodiment of a tensioner for use with the system of FIG. 1 showing that the tensioner includes a strap attachment body configured to be coupled to the strap to maintain a fixed position of the tensioner relative to the arm of the user, a lead screw, and a stepper motor to drive movement of the second end of the strap toward the first end of the strap to tighten the strap on the arm of the user.
Figure 14B:
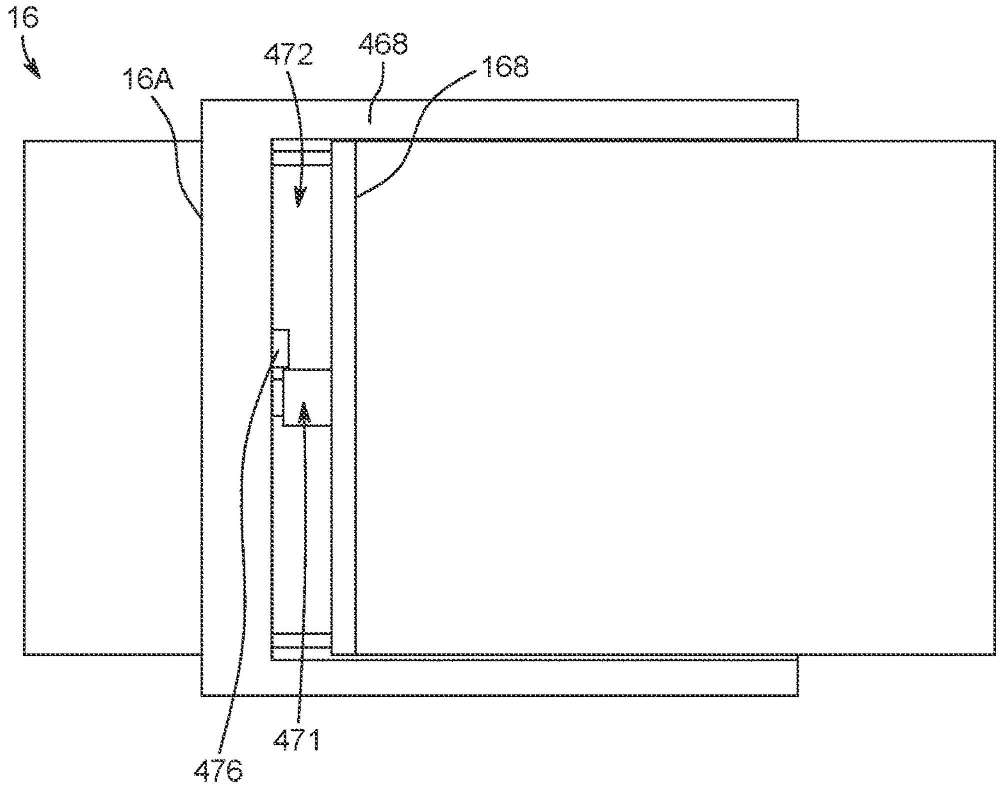
FIG. 14B is a top view of the tensioner of FIG. 14A showing the tensioner and the strap after the second end of the strap is moved toward the first end of the strap to tighten the strap on the arm of the user.

As shown in FIGS. 14A and 14B, the tensioner 418 includes a strap attachment body 468 and an actuator 470. The first end 16A of the strap 16 is coupled to the strap attachment body 468 in a fixed position, and the second end 16B of the strap 16 opposite the first end 16A is coupled to the strap attachment body 468 for movement relative to the strap attachment body 468. The strap attachment body 468 is formed to include a recess 472 to receive the second end 16B of the strap 16 as the second end 16B of the strap 16 moves toward the first end 16A of the strap 16 as suggested in FIGS. 14A and 14B. In response to the instruction, the actuator 470 drives movement of the second end 16B of the strap 16 toward the first end 16A of the strap 16 to decrease the effective length of the strap 16 so that the surface contact pressure data aligns with and/or matches the optimized surface contact pressure.

In some embodiments, the actuator 470 may include a stepper motor 471 and a lead screw 474 as shown in FIG. 14A. As the lead screw 474 rotates about a fixed axis, the second end 16B of the strap 16 moves along the length of the lead screw 474 toward the first end 16A of the strap 16, as shown in FIGS. 14A and 14B. In some embodiments, the tensioner 418 may include at least two limit switches 476. The limit switches 476 are configured to detect and/or sense a location of the second end 16B of the strap 16 to indicate whether the second end 16B of the strap 16 can be tightened or loosened more. The limit switches 476 are configured to define endpoints over which the second end 16B of the strap 16 can move before being stopped.

The system 10 may be used to characterize varying physiological signal data due to blood, known as the AC signal. The quasi-DC component from tissue may be broken down into physiological components, which may be used for classification and increase the utility of the physiological signal data. The system 10 may also dissect portions of the DC component of the physiological signal data.

Feedback from the pressure sensor 20 may provide an improved cardiovascular pulsatile signal-to-noise ratio (SNR) resulting from the optimized surface contact pressure applied to the user by the biosensor 14. Applying specific surface contact pressures to the user may increase physiological signals of interest, such as a heart rate signal from arteries, while suppressing other confounding signals, such as a heart rate signal from arterioles, thereby increasing SNR specific to the physiological signals of interest, such as, but not limited to blood pressure, body fat percentage, and/or hydration levels. Feedback from the pressure sensor 20 allows for amplification and characterization of physiological signals.

At low surface contact pressures, the system 10 can isolate capillary and/or arteriole pressures. The capillary and/or arteriole pressures may be proportionate to blood pressure. Blood pressure may be determined using the surface contact pressure values and performing waveform analysis. Data from the pressure sensor 20 and the biosensor 14 may be used to calculate biological parameters of the user and/or to detect biomarkers for metrics that determine ailments and relative health states of the user.

Figure 16B:
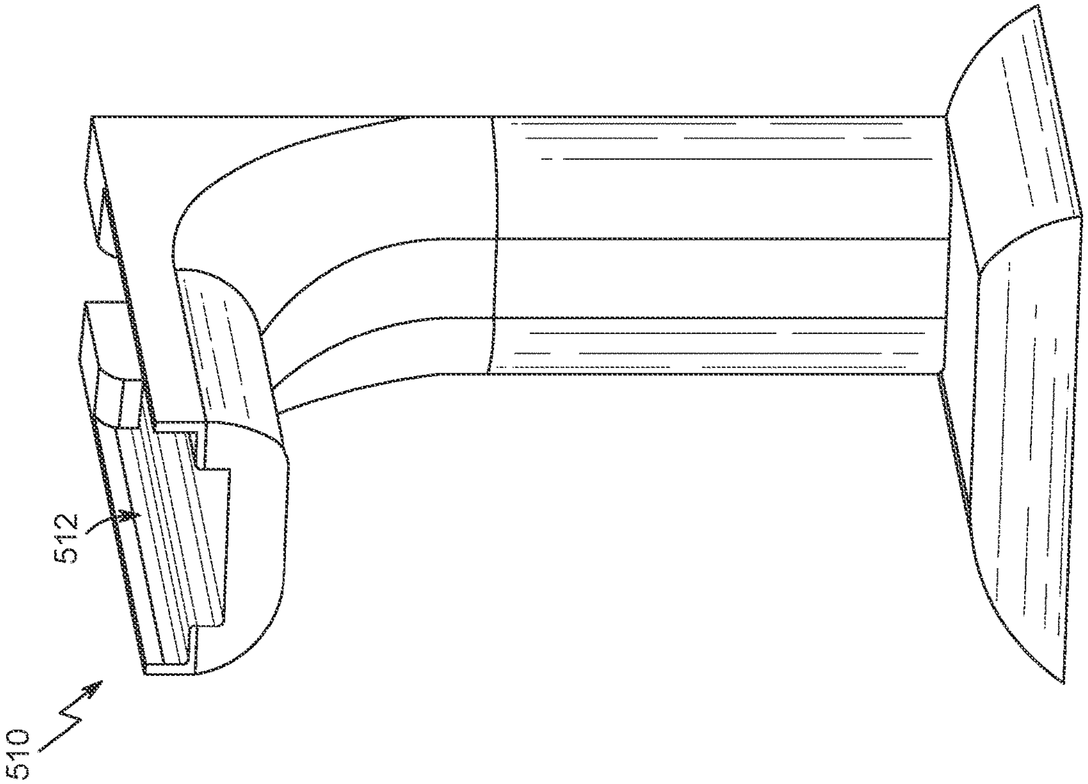
FIG. 16B is a perspective view of the calibration jig of FIG. 16A with the tensioner, the biosensor, and the pressure sensor of FIG. 15 removed from the calibration jig.
Figure 16A:
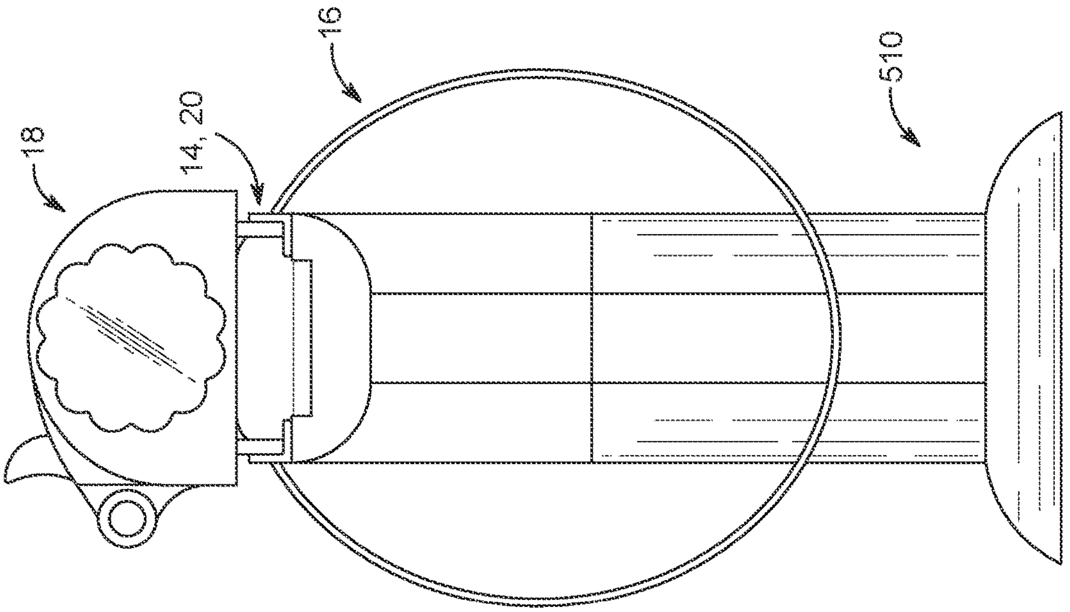
FIG. 16A is a front view of a calibration jig showing that the calibration jig receives the tensioner, the biosensor, and the pressure sensor of FIG. 15 therein to provide a calibration curve.

A calibration jig 510 is provided herein to calibrate the system 10 as shown in FIGS. 16A and 16B. As shown in FIG. 16A, the integrated biosensor 14, tensioner 18, and pressure sensor 20 of FIG. 15 are placed in a cradle 512 of the calibration jig 510. Weights may be placed on the strap 16 to obtain electrical values for each of the associated weights. The values for each of the associated weights may be used to develop a calibration curve. The calibration curve may be programmed into the controller 22. The calibration curve may be configured to offset mechanical variables and hysteresis with the pressure sensor 20.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

What is claimed is:

1. A system comprising a physiological measurement device including a biosensor configured to measure physiological signals upon placement in contact with a user, a strap coupled to the biosensor, and a tensioner that cooperates with the strap to fix a position of the biosensor relative to the user and configured to adjust the strap to establish a surface contact pressure applied to the user by the biosensor when the biosensor is fixed in position relative to the user, a pressure sensor configured to measure the surface contact pressure applied to the user by the biosensor, and a controller in communication with the pressure sensor and the biosensor, the controller configured to output an instruction associated with an optimized surface contact pressure to be implemented via the tensioner, the optimized surface contact pressure based on surface contact pressure data received from the pressure sensor and physiological signal data received from the biosensor so that the instruction can be used for alignment of the surface contact pressure data to the optimized surface contact pressure to manage a level of motion artifact in physiological signals measured by the biosensor thereby yielding improved physiological signal data output from the biosensor.

2. The system of claim 1, wherein the controller is in communication with a user interface; and wherein the controller is configured to output the instruction associated with the optimized surface contact pressure to the user interface so that the user is informed of the optimized surface contact pressure to be implemented via the tensioner by the user.

3. The system of claim 2, wherein the instruction is a visual indicator or an auditory indicator.

4. The system of claim 1, wherein the controller is in communication with the tensioner; and wherein the controller is configured to communicate the instruction associated with the optimized surface contact pressure to the tensioner.

5. The system of claim 4, wherein the tensioner is configured to adjust the strap in response to receiving the instruction from the controller so that the surface contact pressure data aligns with the optimized surface contact pressure.

6. The system of claim 5, wherein the tensioner is configured to provide infinitely variable adjustment of the strap; and wherein the controller is configured to match the surface contact pressure data to the optimized surface contact pressure.

7. The system of claim 1, wherein the pressure sensor is coupled to the strap and the biosensor is coupled to the pressure sensor to locate the biosensor between the user and the pressure sensor.

8. The system of claim 1, wherein the pressure sensor includes one pressure transducer coupled to the biosensor to locate the biosensor between the user and the pressure transducer; and wherein a centerpoint of the pressure transducer is aligned with a centerpoint of the biosensor.

9. The system of claim 1, wherein the tensioner includes a strap attachment body coupled to the strap to maintain a fixed position of the tensioner relative to the user, a tensioner shaft arranged to rotate about a fixed axis, and a tensioning dial configured to be rotated to cause rotation of the tensioner shaft about the fixed axis; and wherein the strap extends around the tensioner shaft so that rotation of the tensioning dial causes an effective length of the strap to decrease to adjust the surface contact pressure applied to the user by the biosensor.

10. The system of claim 9, wherein the tensioner and the biosensor are located on opposing sides of the strap such that a portion of the user is configured to be located between the tensioner and the biosensor.

11. The system of claim 1, wherein the tensioner includes a strap attachment body coupled to the strap to maintain a fixed position of the tensioner relative to the user and an actuator configured to automatically decrease an effective length of the strap to adjust the surface contact pressure applied to the user by the biosensor.

12. A system comprising a physiological measurement device including a biosensor configured to measure physiological signals, a strap coupled to the biosensor, and a tensioner that cooperates with the strap to fix a position of the biosensor relative to the user and configured to adjust the strap to establish a surface contact pressure applied to the user by the biosensor, a pressure sensor configured to measure the surface contact pressure applied to the user by the biosensor, wherein the pressure sensor is coupled directly to the strap and the biosensor is coupled directly to the pressure sensor to locate the biosensor between the user and the pressure sensor, and a controller in communication with the pressure sensor, the controller configured to output an instruction associated with an optimized surface contact pressure to be implemented via the tensioner through adjustment of an effective length of the strap, wherein the optimized surface contact pressure is based, at least in part, on surface contact pressure data received from the pressure sensor and physiological signal data received from the biosensor.

13. The system of claim 12, wherein the controller is in communication with the biosensor; and wherein the instruction associated with the optimized surface contact pressure is based, at least in part, on physiological signal data from the biosensor.

14. The system of claim 12, wherein the controller is in communication with a user interface; and wherein the controller is configured to output the instruction associated with the optimized surface contact pressure to the user interface so that the user is informed of the optimized surface contact pressure to be implemented via the tensioner by the user.

15. The system of claim 12, wherein the controller is in communication with the tensioner; and wherein the controller is configured to communicate the instruction associated with the optimized surface contact pressure to the tensioner.

16. The system of claim 15, wherein the tensioner is configured to adjust the effective length of the strap in response to receiving the instruction from the controller so that the surface contact pressure data aligns with the optimized surface contact pressure.

17. A method of improving physiological signal data output from a biosensor comprising providing a physiological measurement device, a pressure sensor, and a controller in communication with the pressure sensor, the physiological measurement device including a biosensor configured to measure physiological signals and coupled directly to the pressure sensor, a strap coupled directly to the pressure sensor, and a tensioner, measuring a surface contact pressure applied to the user by the biosensor using the pressure sensor, storing surface contact pressure data in a memory of the controller, and generating an instruction associated with an optimized surface contact pressure based, at least in part, on the surface contact pressure data received from the pressure sensor and physiological signal data received from the biosensor.

18. The method of claim 17, further comprising outputting the instruction associated with the optimized surface contact pressure to a user interface.

19. The method of claim 17, further comprising communicating the instruction associated with the optimized surface contact pressure to the tensioner and adjusting an effective length of the strap via the tensioner in response to receiving the instruction from the controller.

* * * * *